United States Patent [19]
Arai

[11] Patent Number: 5,998,370
[45] Date of Patent: Dec. 7, 1999

[54] AGENTS FOR THE PREVENTION AND/OR TREATMENT OF RADIATION-INDUCED DISORDERS BY ADMINISTRATING TCF-II

[75] Inventor: Yoshio Arai, Pittsburgh, Pa.

[73] Assignee: Snow Brand Milk Products Co., Ltd., Hokkaido, Japan

[21] Appl. No.: 09/115,294

[22] Filed: Jul. 14, 1998

[30] Foreign Application Priority Data

Jul. 14, 1997 [JP] Japan .................................. 9-188384

[51] Int. Cl.$^6$ .................................................. A61K 38/18
[52] U.S. Cl. .............................. 514/12; 514/2; 424/579; 424/570; 424/578; 424/572; 424/573

[58] Field of Search .............................. 514/2, 12, 893–4; 530/350, 399

[56] References Cited

U.S. PATENT DOCUMENTS 5,587,359  12/1996  Higashio et al. .......................... 514/12
5,703,048  12/1997  Roos et al. ................................ 514/12

*Primary Examiner*—F. T. Moezie
*Attorney, Agent, or Firm*—Knobbe, Martens, Olson & Bear, LLP

[57] ABSTRACT

The use of Tumor Cytotoxic Factor-II (TCF-II) enables the prevention and/or treatment of radiation-induced disorders.

6 Claims, 2 Drawing Sheets

AGENTS FOR THE PREVENTION AND/OR TREATMENT OF RADIATION-INDUCED DISORDERS BY ADMINISTRATING TCF-II

This application claims priority under 35 U.S.C. § 119 based on JP 9-188384, filed Jul. 14, 1997.

BACKGROUND OF THE INVENTION

1. Field of the Invention

The present invention relates to agents containing Tumor Cytotoxic Factor-II (TCF-II) as an effective component for the prevention and/or treatment of radiation-induced disorders. The present invention provides excellent agents for the prevention and/or treatment of radiation-induced disorders caused by radiation therapy performed to treat diseases such as cancers and acquired immune deficiency syndrome (AIDS). The agents are useful as medicinal preparations.

2. Description of the Related Art

Bone marrow suppression is manifested by reduced platelet count (thrombocytopenia), reduced leukocyte count (leucopenia), and anaemia. Since bone marrow suppression occured as a direct result of chemotherapy and radiation therapy administered for diseases such as cancers and acquired immune deficiency syndrome (AIDS), it has become a serious problem in the treatment of said diseases. At present, only symptomatic treatments such as infusions of erythrocytes and platelets are used to treat the bone marrow suppression caused by these therapies for these diseases. Although the use of Colony Stimulating Factor (CSF) is gaining recognition as a medicinal agent to stimulate the growth of leukocytes to replenish their number, to date no medicinal agent is known which will effectively prevent bone marrow suppression.

Preliminary experiments showed that a certain kind of biologically active substance derived from the body prevented the bone marrow suppression. Examples of such substances include interleukin-1 (IL-1) and macrophage inflammatory protein 1a (MIP-1a) (G. Damia, Cancer Res., 4082–4089, 52, 1992; B. Lord, Blood, 2605–2609, 79, 1992). However, IL-1 has a strong inflammatory action and is concerned to cause side effects such as inflammation and shock including headache and fever (Saito et al., Geka Chiryo (Surgical Therapy), 65, 156–164, 1991). Furthermore, there has been no report on MIP-la other than preliminary experiments.

SUMMARY OF THE INVENTION

As a result of intensive search and study for therapeutic drugs to control radiation-induced disorders, the present inventors have found that TCF-II which is known as a tumor cytotoxic factor has an excellent effect to prevent and treat radiation-induced disorders. Accordingly, an objective of the present invention is to provide an agent containing TCF-II as an effective component to prevent and/or treat radiation-induced disorders which are caused by radiation therapy used in treatments of diseases such as cancer and AIDS.

The present invention relates to agents containing TCF-II as an effective component for the prevention and/or treatment of radiation-induced disorders. The present invention provides agents for the prevention and/or treatment of radiation-induced disorders caused by radiation therapy used in treatments of diseases such as cancers and AIDS. The agents are useful as medicinal preparations.

BRIEF DESCRIPTION OF THE DRAWINGS

In FIG. 1, a solvent was administered to Group I (control group) animals, and TCF-II was administered to Group II animals. A symbol * shows that there is a significant difference between the groups at $p<0.05$.

In FIG. 2, a solvent was administered to Group I (control group) animals, and TCF-II was administered to Group II animals. A symbol * shows that there is a significant difference between the groups at $p<0.05$.

In FIG. 3, a solvent was administered to Group I (control group) animals, and TCF-II was administered to Group II animals.

DETAILED DESCRIPTION OF THE INVENTION AND PREFERRED EMBODIMENTS

Figure 1:
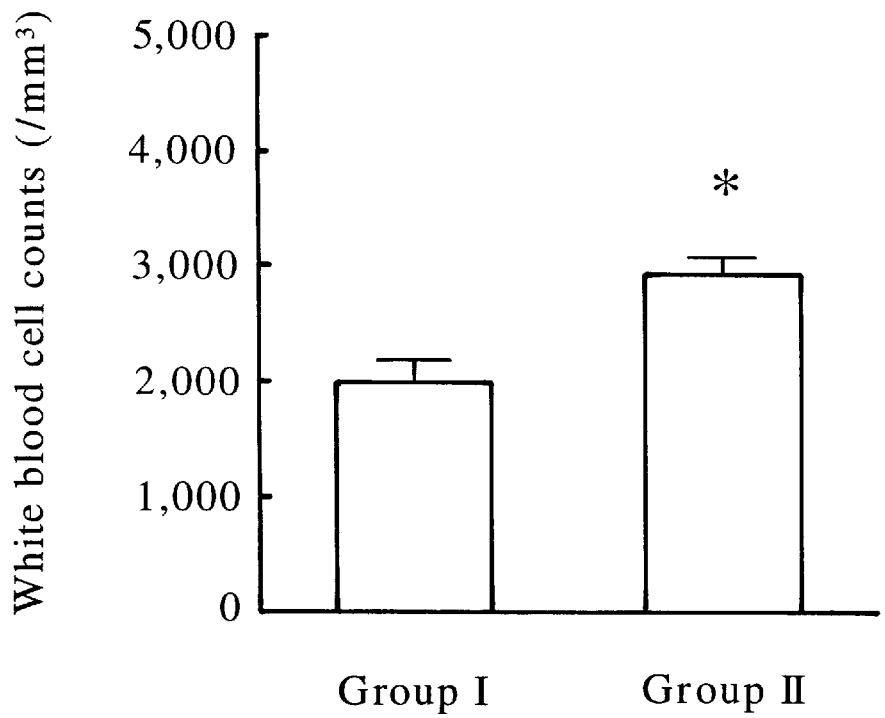
FIG. 1 illustrates the effect of TCF-II in suppressing a decrease in the White Blood Cell counts after irradiation as performed in Example 1.

TCF-II, the effective component of the present invention, is a known protein derived from human fibroblasts and has the following characteristics:
1) Molecular weight (SDS electrophoresis)
   Under non-reduced conditions:
   $78,000 \pm 2,000$ or $74,000 \pm 2,000$
   Under reduced conditions:
   $52,000 \pm 2,000$ (common band A)
   $30,000 \pm 2,000$ (band B)
   $26,000 \pm 2,000$ (band C)
2) Isoelectric point: 7.4–8.6

The abovementioned TCF-II can be obtained by a method in which a liquid culture of human fibroblasts is concentrated and absorbed on an ion exchanger, and the resulting eluate is purified by affinity chromatography (WO 90/10651), or by a genetic engineering technique (WO 92/01053).

TCF-II, the effective component of the present invention, can be a compound derived from human fibroblasts IMR-90, or a compound produced by gene recombination using microorganisms or other cells based on the gene sequence described in WO 90/10651. Alternatively, a compound obtained by a genetic engineering technique disclosed in WO 92/01053 may be used. In all cases, either TCF-II with no bonded sugar chain or TCF-II with different bonded sugar chains produced from different host cells or microorganisms can be used, but the TCF-II with bonded sugar chains is preferable. TCF-II thus obtained can be further concentrated and purified using ordinary isolation and purification methods. For example, a precipitation method using an organic solvent, salting out, gel filtration, affinity chromatography using a monoclonal antibody, or electrophoresis can be used. The method of purification by affinity chromatography using a monoclonal antibody is disclosed in Japanese Patent Laid-open 93/97 and TCF-II can be purified using the monoclonal antibody therein disclosed. Purified TCF-II can be lyophilized or frozen for storage. Moreover, any substance which has an activity similar to TCF-II can be used as an agent similar to that of the present invention. For example, Hepatocyte Growth Factor (HGF) which is different from TCF-II protein in five amino acids (Japanese Patent Laid-open 88/22526) or purified Scatter Factor (SF, Gherardi and Stocker, Nature, 346, 228, 1990) can be used. Furthermore, the agents of the present invention can be used as an adjunct in chemotherapy which, like radiation therapy, induces bone marrow suppression.

The prevention and/or treatment of radiation-induced disorders can be carried out by administering the agents for the prevention and/or treatment of radiation-induced disorders according to the present invention intravenously, or by intramuscular or subcutaneous injection. Pharmaceutical preparations for the prevention and/or treatment of radiation-induced disorders can be produced by mixing pharmacologically acceptable carriers or diluting agents, which are selected according to desired forms, with TCF-II protein as an effective component. These pharmaceutical preparations are produced in accordance with a known pharmaceutical method. If necessary, pH controlling agents, buffering agents, stabilizing agents or the like can be added. The dosage of the pharmaceutical preparations of the present invention to patients is not specifically limited and may vary depending on severity of symptoms, general state of health, age and body weight of the patient to be treated, and other conditions. For example, a pharmaceutical preparation containing 0.6 mg–600 mg, preferably 6 mg–60 mg, of purified TCF-II can be administered to an adult once or more per day. The concentration of TCF-II in pharmaceutical preparations can be determined depending on the amount of administration.

The following production examples and embodiment examples explain the present invention more in detail. However, it should be understood that they are for purpose of illustration only and do not limit the scope of the present invention.

Production Example 1
Purification of TCF-II

Cells were cultured in accordance with the method disclosed in WO 90/10651 and the method of Higashio et al. (Higashio, K., et al., B.B.R.C., Vol. 170, 397–404, 1990) to obtain purified TCF-II. Namely, $3 \times 10^6$ cells of human fibroblast IMR-90 (ATCC CCL-186) were transferred into a roller bottle containing 100 ml of DMEM culture medium supplemented with 5% calf serum and cultured for 7 days at a rolling speed of 0.5–2 rpm. When the total cell count reached $1 \times 10^7$, trypsin was added to peal off the cells and the cells were collected in the bottom of the bottle. 100 g of sterilized 5–9 mesh ceramic particles (Toshiba Ceramic) were put in the bottle, and the cells were statically cultured for 24 hours. Then, 500 ml of the abovementioned medium was added and incubation was continued. The whole medium was recovered and the medium was freshly supplemented at intervals of 7–10 days. In this way, production was continued for 2 months to recover 4 L of fluid culture per roller bottle. Specific activity of the fluid culture thus obtained was 32 μg/ml. 750 L of the fluid culture were concentrated by ultrafiltration using a membrane filter (MW6000 cut, Amicon) and purification was carried out using four steps of chromatography, i.e., CM Sephadex C-50 (Pharmacia), Con A Sepharose (Pharmacia), Mono S Column (Pharmacia) and Heparin Sepharose (Pharmacia) to obtain purified TCF-II.

Production Example 2
Production of Recombinant TCF-II

Cells with a recombinant TCF-II gene were cultured to obtain purified TCF-II in accordance with the method disclosed in WO 92/01053. Transformed Namalwa cells were cultured to obtain 20 L of fluid culture. This fluid culture was sequentially subjected to chromatography on CM Sephadex C-50 (Pharmacia), Con-A Sepharose CL-6B (Pharmacia) and HPLC equipped with Mono S Column (Pharmacia) to obtain about 11 mg of purified TCF-II.

Production Example 3
Production of TCF-II Pharmaceutical Preparations

Examples of the production of injections containing TCF-II obtained in Production Examples 1 and 2 are as follows:

| (1) TCF-II | 20 μg |
|---|---|
| Human serum albumin | 100 mg |

The above ingredients were dissolved in a citric acid buffer solution, pH 6.03, and adjusted to a total volume of 20 ml. The solution was sterilized, dispensed into vials (2 ml each), and then lyophilized, after which the vials were sealed.

| (2) TCF-II | 40 μg |
|---|---|
| Tween 80 | 1 mg |
| Human serum albumin | 100 mg |

The ingredients above were dissolved in a saline solution for injection, and the total volume was made to 20 ml. The solution was sterilized, dispensed into vials (2 ml each), and then lyophilized, after which the vials were sealed.

| (3) TCF-II | 20 μg |
|---|---|
| Tween 80 | 2 mg |
| Sorbitol | 4 g |

The ingredients above were dissolved in a citric acid buffer solution, pH 6.03, and adjusted to a total volume of 20 ml. The solution was sterilized, dispensed into vials (2 ml each), and then lyophilized, after which the vials were sealed.

| (4) TCF-II | 40 μg |
|---|---|
| Tween 80 | 1 mg |
| Glycine | 2 g |

The above ingredients were dissolved in a saline solution for injection, and the total volume was made to 20 ml. The solution was sterilized, dispensed into vials (2 ml each), and then lyophilized, after which the vials were sealed.

| (5) TCF-II | 40 μg |
|---|---|
| Tween 80 | 1 mg |
| Sorbitol | 2 g |
| Glycine | 1 g |

The ingredients above were dissolved in a saline solution for injection and adjusted to a total volume of 20 ml. The solution was sterilized, dispensed into vials (2 ml each), and then lyophilized, after which the vials were sealed.

| (6) TCF-II | 20 g |
|---|---|
| Sorbitol | 4 g |
| Human serum albumin | 50 mg |

The above ingredients were dissolved in a citric acid buffer solution, pH 6.03, and adjusted to a total volume of 20 ml. The solution was sterilized, dispensed into vials (2 ml each), and then lyophilized, after which the vials were sealed.

| (7) TCF-II          | 40 μg |
|---------------------|-------|
| Glycine             | 2 g   |
| Human serum albumin | 50 mg |

The ingredients above were dissolved in a saline solution for injection, and the total volume was made to 20 ml. The solution was sterilized, dispensed into vials (2 ml each), and then lyophilized, after which the vials were sealed.

| (8) TCF-II          | 40 μg |
|---------------------|-------|
| Human serum albumin | 50 mg |

The above ingredients were dissolved in a citric acid buffer solution, pH 6.03, and adjusted to the total volume of 20 ml. The solution was sterilized, dispensed into vials (2 ml each), and then lyophilized, after which the vials were sealed.

Embodiment Example 1
Effect of TCF-II Administration on Bone Marrow Suppression in Radiated Mice A cesium (Cs) 137 irradiator (J L Shepherd and Associates, San Fernando, Calif.) was used for irradiation. The irradiation dose was 5.5 Gy which is known to be a sublethal dose in whole body radiation. One week before the radiation, 12-week-old female C3H/HeJ mice were divided into 2 groups. Group I was a control group in which only solvent was administered to the animals, and Group II was an experimental group in which 500 μg/kg/dose of TCF-II were administered to the animals. TCF-II was administered twice a day for one week.

Figure 2:
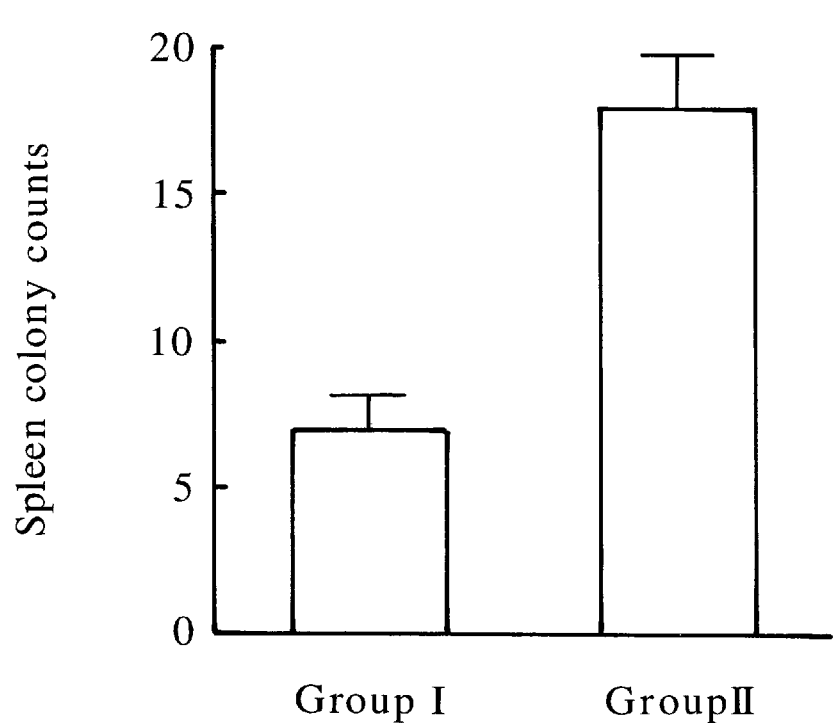
FIG. 2 illustrates the effect of TCF-II in suppressing a decrease in the number of stem cells after irradiation as performed in Example 1.
Figure 3:
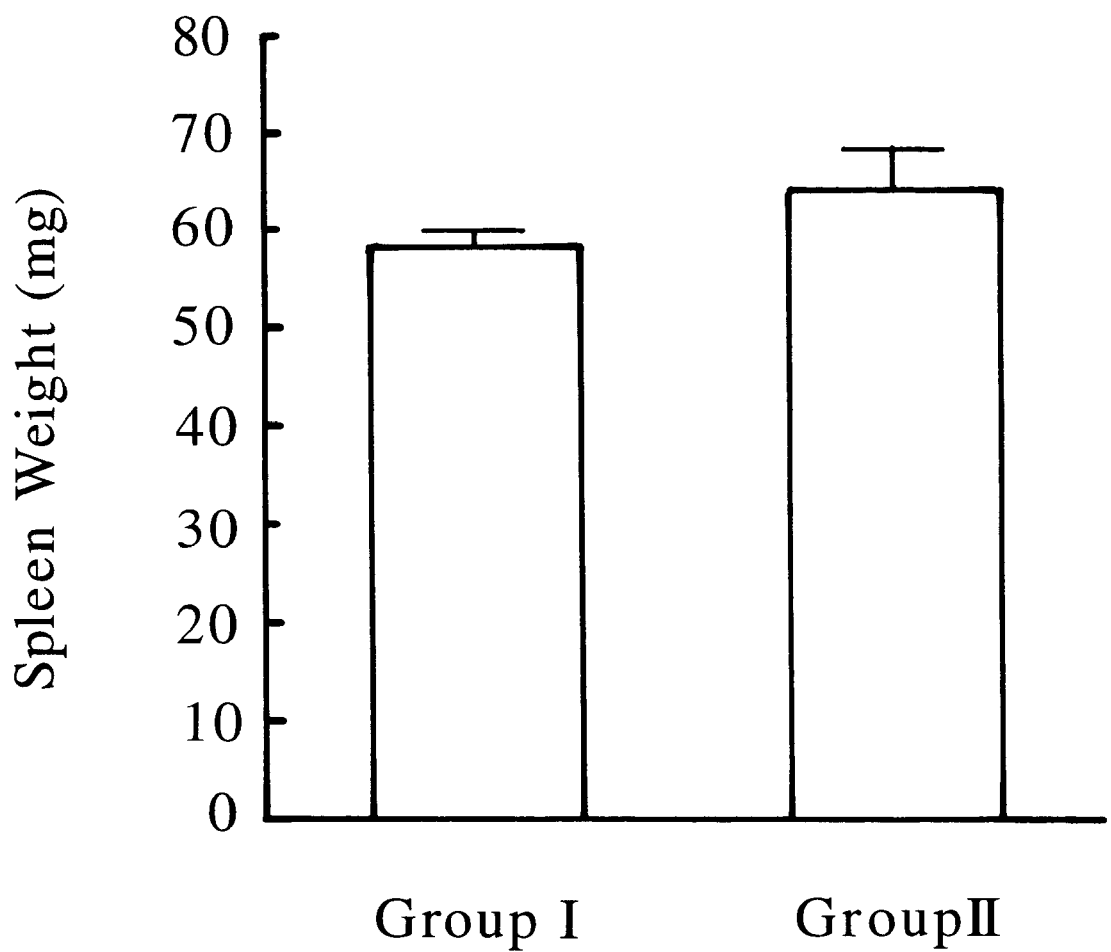
FIG. 3 illustrates the effect of TCF-II in suppressing spleen atrophy after radiation as performed in Example 1.

Nine days after the irradiation, a blood sample was taken and the White Blood Cell counts was determined. The spleen colony counts and the spleen weight were determined 10 days after the irradiation. FIG. 1 shows the result of the White Blood Cell counts. The White Blood Cell counts in animals to which TCF-II was administered (Group II) were significantly higher than those in animals to which the solvent was administered (Group I), indicating that the TCF-II administration suppressed the reduction in the number of leucocytes caused by the irradiation. Next, FIG. 2 shows the result of the spleen colony counts. The numbers of intrinsic spleen colonies in animals to which TCF-II was administered (Group II) were significantly higher than those in animals to which the solvent was administered (Group I), indicating that the TCF-II administration suppressed the reduction in the number of stem cells caused by the irradiation. FIG. 3 shows the result of the determination of the weight of the spleen. The weights of the spleen in animals to which TCF-II was administered (Group II) were higher than those in animals to which the solvent was administered (Group I), indicating that the TCF-II administration tended to suppress the atrophy of the spleen caused by the irradiation. Namely, the TCF-II administration has the marked effect in suppressing radiation-induced disorders such as a decrease in the number of leukocytes and stem cells and the atrophy of the spleen caused by the irradiation.

Thus, the results above showed that the present invention provides excellent agents for the prevention and/or treatment of radiation-induced disorders caused by radiation therapy administered to treat diseases such as cancers and AIDS. The agents are useful as medicinal agents.

What is claimed is:

1. A method for the prevention or treatment of radiation-induced disorders, comprising administrating Tumor Cytotoxic Factor-II to a mammal exposed to or expected to be exposed to radiation in an amount effective to prevent or treat disorders induced by the radiation exposure, said disorders being bone marrow suppression.

2. The method according to claim 1, wherein Tumor Cytotoxic Factor-II is administered in an amount between 0.6 and 600 mg.

3. The method according to claim 1, wherein Tumor Cytotoxic Factor-II is administered in an amount between 6 and 60 mg.

4. A method for the prevention or treatment of radiation-induced disorders, comprising administrating Tumor Cytotoxic Factor-II to a mammal exposed to or expected to be exposed to radiation in an amount effective to prevent or treat disorders induced by the radiation exposure, said disorders being spleen atrophy.

5. The method according to claim 4, wherein Tumor Cytotoxic Factor-II is administered in an amount between 0.6 and 600 mg.

6. The method according to claim 4, wherein Tumor Cytotoxic Factor-II is administered in an amount between 6 and 60 mg.

* * * * *